United States Patent
Lam et al.

[11] Patent Number: 5,945,684
[45] Date of Patent: Aug. 31, 1999

[54] COMPUTER CONTROLLED COLLIMATOR CHANGER

[75] Inventors: Chan F. Lam, Mt. Pleasant; Stephen J. Nelson, Charleston, both of S.C.

[73] Assignee: Medical University of South Carolina Foundation of Research Development

[21] Appl. No.: 08/926,282

[22] Filed: Sep. 5, 1997

[51] Int. Cl.[6] .................................................. H01J 37/00
[52] U.S. Cl. ................................. 250/492.3; 250/492.1; 378/65
[58] Field of Search ........................... 250/492.3, 492.1; 378/65

[56] References Cited

U.S. PATENT DOCUMENTS

| | | | |
|---|---|---|---|
| 3,073,960 | 1/1963 | Guentner et al. | 250/108 |
| 4,172,979 | 10/1979 | Morrison | 250/505 |
| 4,359,642 | 11/1982 | Heinz et al. | 378/150 |
| 4,788,699 | 11/1988 | Dobert et al. | 378/38 |
| 4,827,491 | 5/1989 | Barish | 378/65 |
| 5,396,889 | 3/1995 | Ueda et al. | 128/653.1 |

OTHER PUBLICATIONS

*Physics Original Contribution* entitled Treatment Planning Optimization for Multiple Arcs Stereotactic Radiosurgery Using a Linear Accelerator Chan F. Lam, Ph.D, J.G. Zhu, M.Sc., Jimmy O. Feen, Ph.D. and Joseph M. Jenrette, III, M.D., pub. May 12, 1995.

*Primary Examiner*—Bruce C. Anderson
*Attorney, Agent, or Firm*—Needle & Rosenberg, P.C.

[57] ABSTRACT

An apparatus controls a stereotactic radiosurgery dose applied to an object being treated by a linear accelerator mounted on a gantry. The linear accelerator is capable of generating a beam having a path and a beam centerline, directed toward the object, and the beam is capable of having a plurality of angular positions relative to the object. The apparatus includes a turntable that is rotatable about an axis of rotation and defines a plurality of openings passing therethrough. Each opening has a center and receives therein a beam collimator of a preselected size. The turntable is disposed so that each of the plurality of openings may be rotated to where the center of the opening is coincident with the beam centerline, thereby allowing the beam to pass therethrough. A drive rotates the turntable about the axis of rotation and a sensor determines the angular position of the beam relative to the object. A controller that is responsive to the angular position determining sensor controls the turntable rotating drive so that as the angular position of the beam relative to the object changes, a preselected collimator is in the path of the beam.

19 Claims, 4 Drawing Sheets

COMPUTER CONTROLLED COLLIMATOR CHANGER

BACKGROUND OF THE INVENTION

1. Field of the Invention

The present invention relates to radiosurgery and, more specifically, to devices for collimating a beam used in radiosurgery.

2. Description of the Prior Art

As shown schematically in FIGS. 1A–1C, prior art radiosurgery systems that are used to irradiate a mass 4 (such as a tumor, or other diseased tissue) in a body 2 (such as a patient's body) with a high-energy beam 6 employ a gantry-mounted linear accelerator 8 capable of traveling along an arcuate path 10. The linear accelerator 8 directs the beam 6 toward the mass 4 from several different angles and, thus, the mass 4 presents several aspects in relation to the beam 6. For example, when the linear accelerator 8 is in relation to the mass 4 as shown in FIG. 1A, the mass 4 presents its broadest aspect to the beam 6. When the linear accelerator 8 travels along the arcuate path 10, as shown in FIG. 1B, the mass 4 presents a narrower aspect in relation to the beam 6. At some point of travel by the linear accelerator 8 along the path 10, the mass 4 presents its narrowest aspect in relation to the beam 6, as shown in FIG. 1C.

With conventional radiosurgery systems, the beam 6 is collimated so that its is wide enough to irradiate the entire mass 4 and the beam 6 maintains a constant width, regardless of the position of the linear accelerator 8 along the path 10. Thus, when the linear accelerator 8 is in the relation to the mass 4 shown in FIG. 1A, only a narrow portion of the beam 6 unnecessarily irradiates healthy tissue 12' within the body 2. However, as the linear accelerator 8 is in the relation to the mass 4 shown in FIG. 1B, a wider portion of the beam 6 unnecessarily irradiates healthy tissue 12". Once the linear accelerator 8 is in a position along the path 10 where the mass 4 presents its narrowest aspect, as shown in FIG. 1C, a considerable portion of the beam 6 unnecessarily irradiates a substantial amount of healthy tissue 12'''.

Unnecessary irradiation of healthy tissue can cause serious harm to the healthy tissue. Therefore, prior art systems have the disadvantage of unnecessarily irradiating substantial amounts of healthy tissue when the relationship of the linear accelerator to the body is such that the mass being irradiated presents a narrow aspect to the beam.

Prior art systems may be stopped periodically to change the collimation of the beam to reflect the current aspect of the mass. However, doing so would introduce the disadvantage of interrupting the treatment process.

SUMMARY OF THE INVENTION

The disadvantages of the prior art are overcome by the present invention which, in one aspect, is an apparatus for controlling a stereotactic radiosurgery dose applied to an object being treated by a linear accelerator mounted on a gantry. The linear accelerator is capable of generating a beam, having a path and a beam centerline, directed toward the object. The beam is capable of having a plurality of angular positions relative to the object. The apparatus includes a turntable that is rotatable about an axis of rotation and defines a plurality of openings passing therethrough. Each opening has a center and receives therein a beam collimator of a preselected size. The turntable is disposed so that each of the plurality of openings may be rotated to where the center of the opening is coincident with the beam centerline, thereby allowing the beam to pass therethrough. A drive mechanism rotates the turntable about the axis of rotation and a sensor determines the angular position of the beam relative to the object. A controller that is responsive to the angular position determining sensor controls the turntable rotating drive so that as the angular position of the beam relative to the object changes, a preselected collimator is in the path of the beam. The position controlling circuit could comprise, for example, a digital computer programmed to place a preselected collimator in the path of the beam as a function of the angular position of the beam relative to the object. An analog circuit could also be employed.

A device that determines the position of the turntable, thereby determining which of the collimators is in the path of the beam, may also be included. Such a device could include an optical sensor affixed to the frame adjacent the outer edge of the turntable and an indicator that indicates to the optical sensor that a selected portion of the outer edge of the turntable is adjacent the optical sensor.

A device that maintains the turntable in a fixed position relative to the frame for a predetermined period may also be included. The position maintaining device could include a plurality of spaced-apart notches defined by the outer edge of the turntable and a solenoid affixed to the frame, the solenoid having a plunger that is engageable with each of the plurality of notches, so that when the plunger is engaged in a selected notch, the turntable is maintained in a fixed position relative to the frame.

In yet another aspect, the invention also includes a method of for controlling a stereotactic radiosurgery dose in which a beam is directed toward a tissue mass in an object, so as to minimize exposure of healthy tissue to the beam. The beam is directed through a first collimator while the object is in a first angular position relative to the beam, so that the beam has a first predetermined shape corresponding to the first angular position of the object relative to the beam. Then the beam is directed through a second collimator while the object is in a second angular position relative to the beam, so that the beam has a second predetermined shape, different from the first predetermined shape, corresponding to the second angular position of the object relative to the beam. The first predetermined shape corresponds to a shape of the tissue mass presented to the beam while the object is in the first angular position and the second predetermined shape corresponds to a shape of the tissue mass presented to the beam while the object is in the second angular position.

With the invention, the collimator can be changed automatically during treatment according to the size specified by an optimal dose treatment plan for different arcs in a multi-arc treatment plan, or for different segments in a dynamic treatment plan. Before radiosurgery begins, the various collimators specified in an optimal treatment plan will be manually or automatically loaded onto a collimator changer. The collimator changer is attached to a gantry so that the appropriate collimator can be automatically switched into place at the proper arc or sub-arc of a multi-arc plan or at the proper segment in a dynamic plan.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1A:
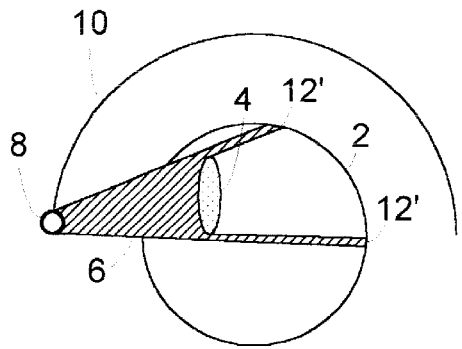
FIGS. 1A–1C are schematic diagrams that conceptually represent prior art radiosurgery systems.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: "a," "an," and "the" includes plural reference, "in" includes "in" and "on."

Figure 1B:
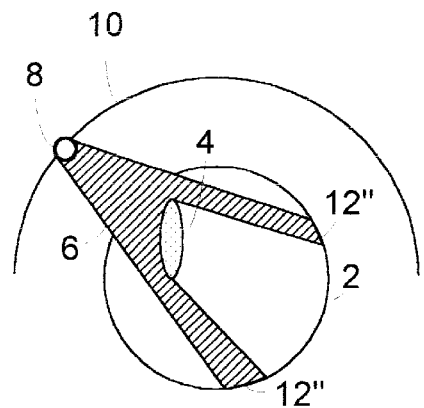
Figure 1C:
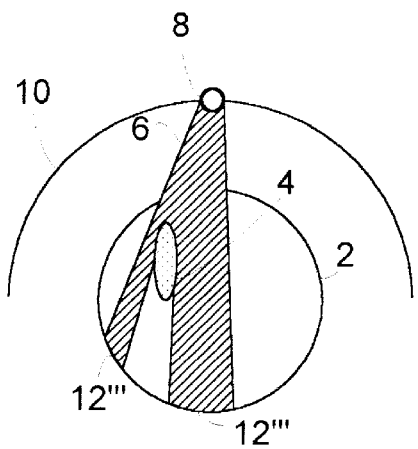
Figure 2A:
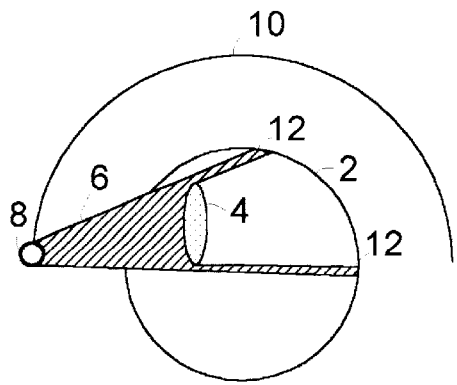
FIGS. 2A–2C are schematic diagrams that conceptually represent a radiosurgery system in accordance with the invention.
Figure 2B:
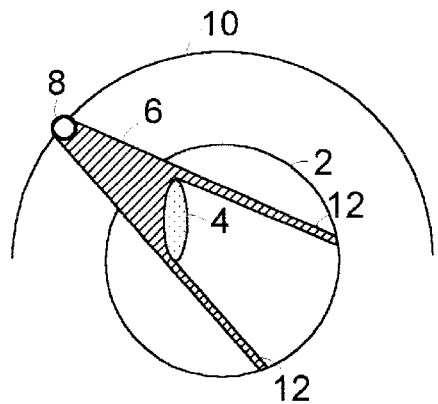
Figure 2C:
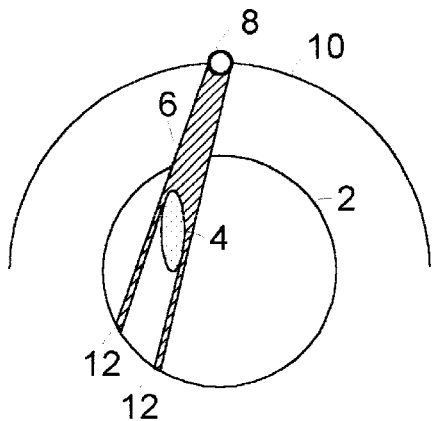

As shown in FIGS. 2A–2C, the present invention comprises a radiosurgery system that is used to irradiate a mass 4 (such as a tumor, or other diseased tissue) in a body 2 (such as a patient's body) with a high-energy beam 6. The system employs a gantry-mounted linear accelerator 8 capable of traveling along an arcuate path 10. Unlike prior art systems (as discussed with reference to FIGS. 1A–1C, above), the present invention employs a device that adjusts collimation of the beam 6, depending on the angular position of the body 2 relative to beam 6 so that only a minimum amount of healthy tissue 12 is unnecessarily irradiated by the beam 6. For example, when a broad aspect of the mass 4 is presented to the beam 6, as shown in FIG. 2A, a collimator is used so that the beam 6 is relatively wide. As the linear accelerator moves through the positions shown in FIG. 2B to FIG. 2C, a progressively narrower collimator is employed to produce a progressively narrower beam 6. In this way, the amount of healthy tissue 12 that is exposed to the beam is minimized.

Figure 3:
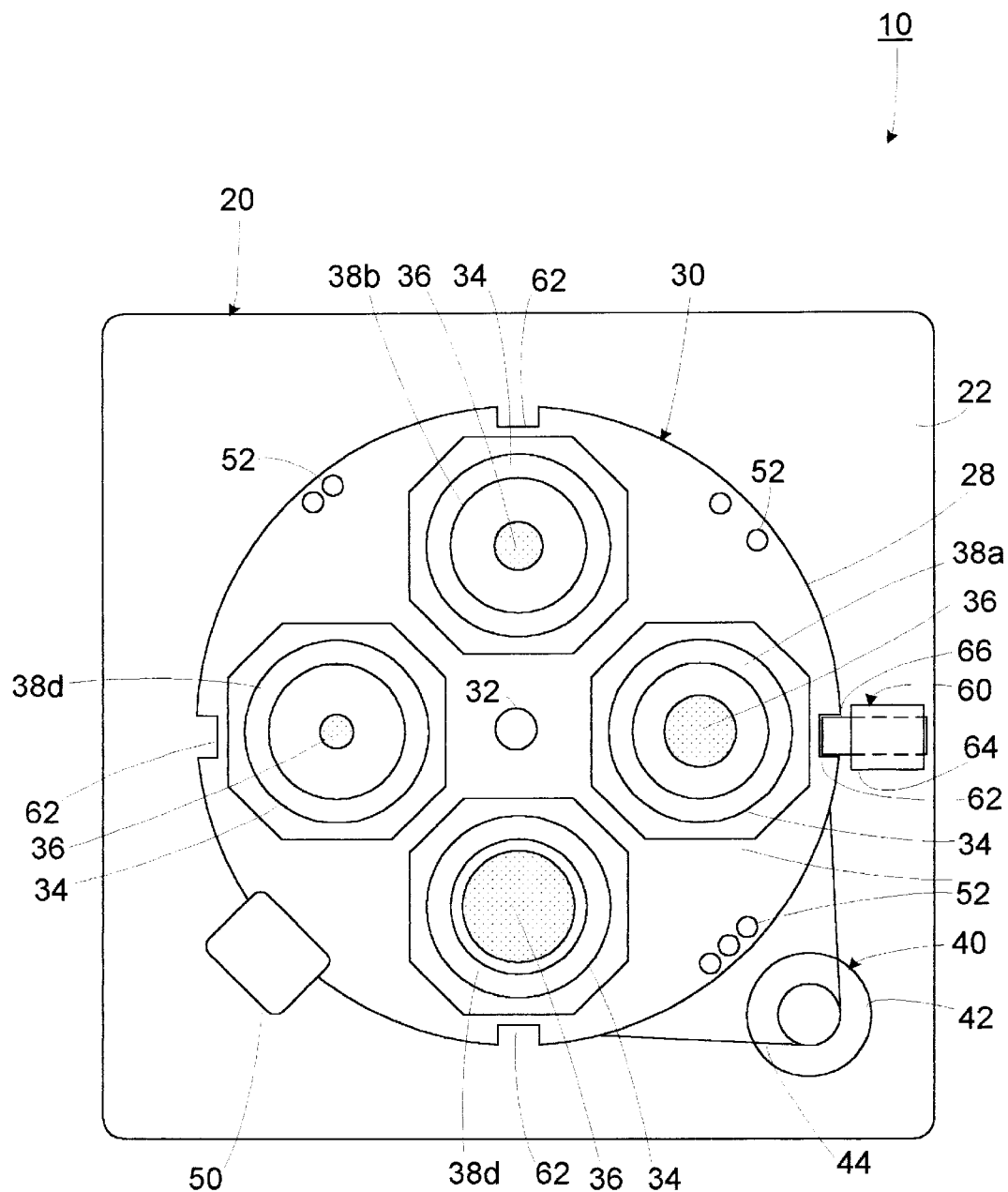
FIG. 3 is a plan view of a collimator changer.

As shown in FIG. 3, the invention 10 includes a collimator changer 20 used to adjust collimation of the beam 6. The collimator changer 20 includes a frame 22 which is affixed to the linear accelerator (not shown in FIG. 3). Rotatably mounted on the frame 22 is a turntable 30, having an outer edge 28. The turntable 30 is rotatable about an axis of rotation 32 and defines a plurality of openings 34 passing therethrough, with each opening having a center 36. Placed in each opening 34 is a beam collimator 38a–d of a preselected size. The sizes of the collimators 38a–d usually increase in order from 38a through 38d, although it is conceivable that in certain treatment plans, the collimators 38a–d will not be ordered by size. The turntable 30 is disposed so that each of the plurality of openings 34 may be rotated to where the center 36 of each opening 34 is coincident with the beam centerline (not shown in FIG. 3), thereby allowing the beam to pass through one of the collimators 34 at a time.

A drive mechanism 40 rotates the turntable 30 about the axis of rotation 32. The drive mechanism 40 could comprise a drive motor 42 coupled to a belt 44 that is also coupled about the turntable 30. The drive mechanism 40 could also include a drive motor 42 coupled to the turntable 30 via a friction wheel, a gear assembly, a sprocket and chain assembly, or by using other conventional drive mechanisms.

An optical sensor 50, affixed to the frame 22 adjacent the outer edge 52 of the turntable 30, determines the position of the rotational turntable 30 and thereby determines which of the collimators 38a–d is in the path of the beam. A plurality of spaced-apart markings indicate to the optical sensor that a selected portion of the outer edge 52 of the turntable 30 is adjacent the optical sensor 50. Other conventional feed-back systems could be employed to indicate the rotational position of the turntable 30, such as a magnetic character reader or an electrical switch mechanism.

The turntable 30 is maintained in a fixed position relative to the frame for a predetermined period by employing a locking mechanism 60. This ensures that the selected collimator 38 is held in the proper orientation during an irradiation cycle. The locking mechanism 60 includes a plurality of spaced-apart notches 62 defined by the outer edge 28 of the turntable that are engaged by a plunger 66. The plunger 66 is driven by a solenoid 64 that is affixed to the frame 22. When the plunger 66 is engaged in a selected notch 62, the turntable 30 is maintained in a fixed position relative to the frame 22. Other mechanisms could be used to positively engage the turntable 30, such as a brake assembly or a gear drive (not shown).

Figure 4:
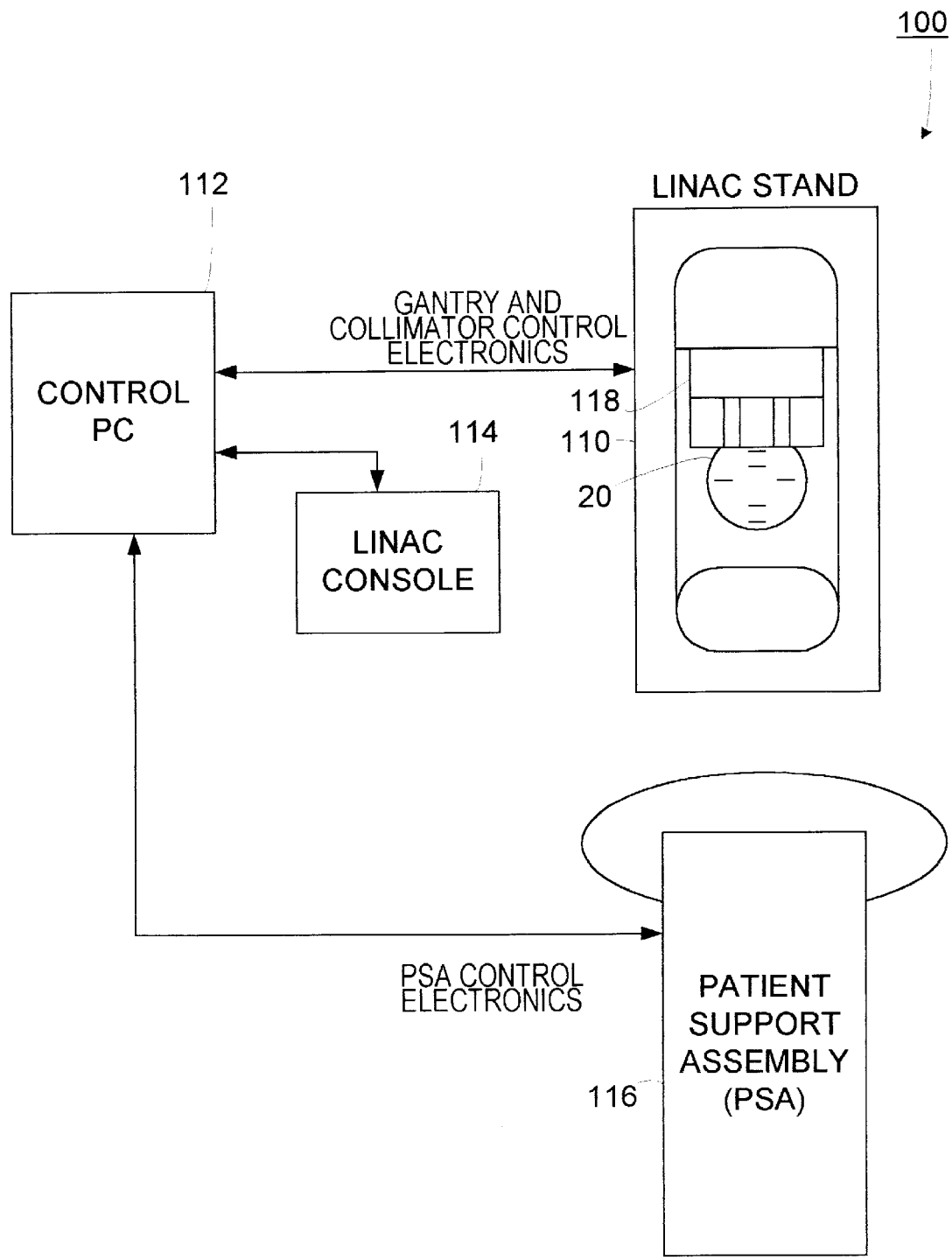
FIG. 4 is a schematic diagram of a radiosurgery system employing a collimator changer.

As shown in FIG. 4, a complete system 100 in accordance with the invention, includes a gantry-type linear accelerator stand 110 that supports a linear accelerator 118 (such as a LINAC) with a collimator changer 20 affixed thereto. A patient support assembly 116 is provided to support and adjust the orientation of the patient. A computer 112, such as a personal computer, controls the functions of the gantry-mounted linear accelerator stand 110, the collimator changer 20 and the patient support assembly 116. For example, the computer 112 could control the speed of rotation and the angle of rotation of both the gantry-type linear accelerator stand 110 and the patient support assembly 116. A console 114 provides an operator interface to the computer 112.

The locking mechanism 60 may be provided with a micro switch that is used to sense the positive engagement of the plunger 66 with the computer 112 being responsive to the position locking mechanism 60. Thus, the computer 112 is able to restrict energization of the linear accelerator 118 to only when the position of the collimator has been verified.

The computer 112 is also responsive to a sensor in the linear accelerator that determines the angular position of the linear accelerator 118, and thus the beam, relative to an object (not shown) on the patient support assembly 116. Angular position of the linear accelerator 118 is determined by a feedback circuit that generates a feedback control signal indicating a spacial relationship of the linear accelerator 118 relative to the object or by a timer that times movement of the object relative to the linear accelerator 118. The computer 112 also controls the position of the turntable 30, so that as the angular position of the beam relative to the object changes, a preselected collimator 38 is in the path of the beam, in accordance with a beam size treatment plan. The computer 112 could also control beam weight by controlling the monitor unit per degree value of the linear accelerator 118.

Generally, the computer 112 could monitor the following: the rotation angle of the patient support assembly 116, the on/off status of the beam, verification of the selected collimator, whether the collimator is in place, and the gantry rotation angle. The computer 112 could control the following: the speed and direction of the patient support assembly 116, energization of the beam, selection of collimator, speed and direction of the collimator changer 20, and gantry rotation speed.

The beam size treatment plan is determined prior to treatment based on a characterization of the mass to be treated and the relevant collimator sizes are entered into the computer.

In an alternate embodiment, the invention could include collimators that adjust the shape of the beam, rather than just the size of the beam. In this way, the collimators could be adjusted so that the shape of the beam conforms closely to the shape of the mass being irradiated. In yet another embodiment, the computer 112 could control the strength of the beam, to allow different intensities of radiation to be delivered to the mass at different angles.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. An apparatus for controlling a stereotactic radiosurgery dose applied to an object being treated by a linear accelerator mounted on a gantry, the linear accelerator capable of generating a beam having a path and a beam centerline, directed toward the object, the beam capable of having a plurality of angular positions relative to the object, comprising:
    a. a turntable, rotatable about an axis of rotation and defining a plurality of openings passing therethrough, each opening capable of receiving therein a beam collimator of a preselected size, each opening having a center, the turntable disposed so that each of the plurality of openings may be rotated to where the center of the opening is coincident with the beam centerline, thereby allowing the beam to pass therethrough;
    b. means for rotating the turntable about the axis of rotation;
    c. an angular position detector that determines the angular position of the beam relative to the object; and
    d. a computer, responsive to the angular position detector, that controls the turntable rotating means so as to control the position of the turntable, the computer being programmed to place a preselected collimator in the path of the beam so that the beam has a beam size that is a function of the angular position of the beam relative to the object according to a beam size treatment plan.

2. The apparatus of claim 1, wherein the beam has a beam weight, the apparatus further comprising means for controlling the beam weight as the beam changes angular position relative to the object.

3. The apparatus of claim 1, further comprising a frame, the turntable having an outer edge and being rotatably mounted on the frame which is fixed in relation to the linear accelerator.

4. The apparatus of claim 3, further comprising means for determining the position of the turntable, thereby determining which of the collimators is in the path of the beam.

5. The apparatus of claim 4, wherein the determining means comprises:
    a. an optical sensor affixed to the frame adjacent the outer edge of the turntable; and
    b. means for indicating to the optical sensor that a selected portion of the outer edge of the turntable is adjacent the optical sensor.

6. The apparatus of claim 3, wherein the maintaining means comprises:
    a. a plurality of spaced-apart notches defined by the outer edge of the turntable; and
    b. a solenoid affixed to the frame, the solenoid having a plunger that is selectively engageable with each of the plurality of notches, so that when the plunger is engaged in a selected notch, the turntable is maintained in a fixed position relative to the frame.

7. The apparatus of claim 1, wherein the rotating means comprises a drive motor affixed to the frame and coupled to the turntable so as to cause rotation of the turntable.

8. The apparatus of claim 1, wherein the angular position determining means comprises:
    a. an angular position sensor capable of sensing the angular position of the beam relative to the object; and
    b. a feedback circuit, responsive to the angular position sensor, that generates a feedback control signal indicating a spacial relationship of the linear accelerator relative to the object.

9. The apparatus of claim 1, wherein the angular position determining means comprises a timer that times movement of the beam relative to the object.

10. An apparatus for performing stereotactic radiosurgery on an object, comprising:
    a. a linear accelerator mounted on a gantry, the linear accelerator capable of generating a beam, having a path and a beam centerline, directed toward the object, the beam capable of having a plurality of angular positions relative to the object;
    b. a frame;
    c. a turntable, having an outer edge, rotatably mounted on the frame in fixed relation to the linear accelerator, the turntable being rotatable about an axis of rotation and defining a plurality of openings passing therethrough, each opening for receiving therein a beam collimator of a preselected size, each opening having a center, the turntable disposed so that each of the plurality of openings may be rotated to where the center of the opening is coincident with the beam centerline, thereby allowing the beam to pass therethrough;
    d. means for rotating the turntable about the axis of rotation;
    e. an angular position detector that determines the angular position of the beam relative to the object; and
    f. a digital computer, responsive to the angular position detector, that controls the turntable rotating means so as to control the position of the turntable, the computer being programmed to place a preselected collimator in the path of the beam so that the beam has a beam size that is a function of the angular position of the beam relative to the object according to a beam size treatment plan.

11. The apparatus of claim 10, further comprising means for determining the position of the turntable, thereby determining which of the collimators is in the path of the beam.

12. The apparatus of claim 11, wherein the determining means comprises:
    a. an optical sensor affixed to the frame adjacent the outer edge of the turntable; and
    b. means for indicating to the optical sensor that a selected portion of the outer edge of the turntable is adjacent the optical sensor.

13. The apparatus of claim 10, wherein the maintaining means comprises:
    a. a plurality of spaced-apart notches defined by the outer edge of the turntable; and
    b. a solenoid affixed to the frame, the solenoid having a plunger that is engageable with each of the plurality of notches, so that when the plunger is engaged in a selected notch, the turntable is maintained in a fixed position relative to the frame.

14. The apparatus of claim 10, wherein the rotating means comprises a drive motor affixed to the frame and coupled to the turntable so as to cause rotation of the turntable.

15. The apparatus of claim 10, wherein the angular position determining means comprises a feedback circuit that generates a feedback control signal indicating a spacial relationship of the linear accelerator relative to the object.

16. The apparatus of claim 10, wherein the angular position determining means comprises a timer that times movement of the object relative to the linear accelerator.

17. The apparatus of claim 10, wherein the position controlling means comprises a digital computer programmed to place a preselected collimator in the path of the beam as a function of the angular position of the beam relative to the object.

18. A method of controlling a stereotactic radiosurgery dose in which a beam is directed toward a tissue mass in an object, so as to minimize exposure of healthy tissue to the beam, comprising the steps of:

a. directing the beam having path through a first collimator while the object is in a first angular position relative to the beam, so that the beam has a first predetermined shape corresponding to the first angular position of the object relative to the beam; and b. directing the beam through a second collimator while the object is in a second angular position relative to the beam, so that the beam has a second predetermined shape, different from the first predetermined shape, corresponding to the second angular position of the object relative to the beam, so that the first predetermined shape corresponds to a shape of the tissue mass presented to the beam while the object is in the first angular position and so that the second predetermined shape corresponds to a shape of the tissue mass presented to the beam while the object is in the second angular position;

c. determining whether the object is in the first angular position or the second angular position using an angular position detector; and d. using a digital computer, responsive to the angular position detector, to place the first collimator in the path of the beam when the object is in the first angular position, and to place the second collimator in the path of the beam when the object is in the second angular position.

19. The method of claim 18, wherein the first collimator and second collimator are mounted on a turntable rotatably disposed so that the beam can be selectively directed through either the first collimator or the second collimator by rotating the turntable until a selected collimator is in the path of the beam, the method further comprising the step of automatically rotating the turntable, thereby changing the collimator in the path of the beam from the first collimator to the second collimator, as the beam changes angular position from the first angular position to the second angular position.

* * * * *